United States Patent
Dieringa

(10) Patent No.: US 11,969,482 B2
(45) Date of Patent: Apr. 30, 2024

(54) RESORBABLE IMPLANT MATERIAL MADE FROM MAGNESIUM OR A MAGNESIUM ALLOY

(71) Applicant: Helmholtz-Zentrum Geesthacht Zentrum für Material- und Küstenforschung GmbH, Geesthacht (DE)

(72) Inventor: Hajo Dieringa, Lüneburg (DE)

(73) Assignee: Helmholtz-Zentrum hereon GmbH, Geesthacht (DE)

(*) Notice: Subject to any disclaimer, the term of this patent is extended or adjusted under 35 U.S.C. 154(b) by 1160 days.

(21) Appl. No.: 16/626,619

(22) PCT Filed: Apr. 23, 2019

(86) PCT No.: PCT/EP2019/060326
§ 371 (c)(1),
(2) Date: Dec. 26, 2019

(87) PCT Pub. No.: WO2019/211121
PCT Pub. Date: Nov. 7, 2019

(65) Prior Publication Data
US 2020/0129642 A1    Apr. 30, 2020

(30) Foreign Application Priority Data
May 3, 2018 (EP) .................... 18170669

(51) Int. Cl.
*A61K 49/00* (2006.01)
*A61L 27/04* (2006.01)
(Continued)

(52) U.S. Cl.
CPC ........ *A61K 49/005* (2013.01); *A61K 49/0067* (2013.01); *A61L 27/047* (2013.01);
(Continued)

(58) Field of Classification Search
CPC . A61K 49/005; A61K 49/0067; A61L 27/047; A61L 27/08; A61L 27/427;
(Continued)

(56) References Cited

U.S. PATENT DOCUMENTS 9,259,516 B2    2/2016  Bayer
9,676,026 B2    6/2017  Witte et al.
(Continued)

FOREIGN PATENT DOCUMENTS

DE    102005060203 A1    6/2007
DE    102016007176 A1    1/2017
(Continued)

OTHER PUBLICATIONS

International Search Report dated Jul. 17, 2019 in corresponding PCT application No. PCT/EP2019/060326.
(Continued)

*Primary Examiner* — Paul B Prebilic
(74) *Attorney, Agent, or Firm* — NIELDS, LEMACK & FRAME, LLC

(57) ABSTRACT

The present invention relates to a resorbable implant material made of magnesium or magnesium alloy and to a process for the production thereof. A disadvantage of the known resorbable implants is that their resorption has hitherto only been trackable using x-ray or CT examinations. The invention provides a resorbable implant material comprising homogeneously distributed fluorescent nanodiamonds in a matrix of magnesium or a magnesium alloy. Fluorescent nanodiamonds are biologically nonhazardous and provide a stable emission in the near infrared range due to nitrogen-vacancy centers (NV centres). This allows detection of the implant material in the blood plasma of the patient.
The resorbable implant material according to the invention is produced by a process wherein magnesium or a magne-
(Continued)

sium alloy is melted, nanodiamonds are added to the melt and the melt of magnesium or a magnesium alloy provided with nanodiamonds is subjected to an ultrasound treatment.

21 Claims, 1 Drawing Sheet

(51) Int. Cl.
| | |
|---|---|
| *A61L 27/08* | (2006.01) |
| *A61L 27/42* | (2006.01) |
| *A61L 27/58* | (2006.01) |
| *A61L 31/02* | (2006.01) |
| *A61L 31/12* | (2006.01) |
| *A61L 31/14* | (2006.01) |
| *C22C 1/02* | (2006.01) |
| *C22C 23/00* | (2006.01) |

(52) U.S. Cl.
CPC ............. *A61L 27/08* (2013.01); *A61L 27/427* (2013.01); *A61L 27/58* (2013.01); *A61L 31/022* (2013.01); *A61L 31/024* (2013.01); *A61L 31/124* (2013.01); *A61L 31/148* (2013.01); *C22C 1/02* (2013.01); *C22C 23/00* (2013.01)

(58) Field of Classification Search
CPC ...... A61L 27/58; A61L 31/022; A61L 31/024; A61L 31/124; A61L 31/148; C22C 1/02; C22C 23/00
See application file for complete search history.

(56) References Cited

U.S. PATENT DOCUMENTS

| | | | |
|---|---|---|---|
| 2004/0043053 A1* | 3/2004 | Yu ........................... | A61L 27/10 424/426 |
| 2011/0172724 A1 | 7/2011 | Hort et al. | |
| 2014/0065424 A1 | 3/2014 | Boudou et al. | |
| 2015/0079148 A1* | 3/2015 | Zhou ....................... | C22C 23/06 424/426 |
| 2015/0238125 A1* | 8/2015 | Acosta ................... | A61B 5/681 600/310 |
| 2020/0032372 A1 | 1/2020 | Bayer et al. | |
| 2020/0114048 A1* | 4/2020 | Dieringa ................ | A61L 31/18 |

FOREIGN PATENT DOCUMENTS

| | | |
|---|---|---|
| DE | 102016119227 A1 | 4/2018 |
| EP | 2318057 B1 | 3/2015 |
| EP | 2198898 B1 | 1/2018 |
| WO | 2010/110919 A1 | 9/2010 |
| WO | 2013/158869 A2 | 10/2013 |
| WO | 2015/144439 A1 | 10/2015 |
| WO | 2017/108655 A1 | 6/2017 |

OTHER PUBLICATIONS

Bolshedvorskii et al., "Single Bright NV Centers in Aggregates of Detonation Nanodiamonds", Optical Materials Express, vol. 7, No. 11, Nov. 1, 2017.
Bradac et al., "Observation and Control of Blinking Nitrogen-Vacancy Centres in Discrete Nanodiamonds", Nature Nanotechnology, vol. 5, Apr. 11, 2010, pp. 345-349.
Chang et al., "Counting Vacancies and Nitrogen-Vacancy Centers in Detonation Nanodiamond", Nanoscale, vol. 8, 2016. pp. 10548-10552.
Dieringa et al., "Ultrasonic Stirring as a Production Process for Nanoparticle Reinforced Magnesium Alloys and the Compression Creep Response of ZE10 Reinforced with Ceria Nanoparticles" 15th European Conference on Composite Materials, pp. 1-8, Jun. 24-28, 2012.
Fu et al., "Characterization and Application of Single Fluorescent Nanodiamonds as Cellular Biomarkers", PNAS vol. 104, No. 3, Jan. 16, 2007, pp. 727-732.
Merchant et al., "Fluorescent Nanodiamonds for Molecular and Cellular Bioimaging", IEEE Journal of Selected Topics in Quantum Electronics, vol. 22, No. 3, May/Jun. 2016.
European communication, with English translation, dated Nov. 6, 2018 in corresponding European patent application No. 18170669. 8, (considered on Jan. 12, 2024).
Dieringa et al., "Ultrasound Assisted Casting of an AM60 Based Metal Matrix Nanocomposite, Its Properties, and Recyclability", Metals, vol. 7, No. 338, Sep. 2017.
Gong et al., "Fabrication, Biodegradation Behavior and Cytotoxicity of Mg-nanodiamond Composites for Implant Application", Journal of Materials Science: Materials in Medicine, vol. 26, No. 110, Feb. 2015.
Reineck et al., "Bright and Photostable Nitrogen-Vacancy Fluorescence from Unprocessed Detonation Nanodiamond", Nanoscale, vol. 9, No. 2, pp. 497-502, Jan. 2017.
Say et al., "Luminescent Nanodiamonds for Biomedical Applications", Biophysical Reviews, vol. 3, pp. 171-184, Dec. 2011.
Treussart et al., "Photoluminescence of Single Colour Defects in 50 nm Diamond Nanocrystals", Physica B Condensed Matter, vol. 376, pp. 926-929, Apr. 2006.
Vaijayanthimala et al., "The Long-term Stability and Biocompatibility of Fluorescent Nanodiamond as an in vivo Contrast Agent", Biomaterials, vol. 33, pp. 7794-7802, Nov. 2012.
Wolff et al., "Magnesium Powder Injection Moulding for Biomedical Application" Powder Metallurgy, vol. 57, No. 5, pp. 331-340, Dec. 2014.
Zhang et al., "Fluorescent PLLA-Nanodiamond Composites for Bone Tissue Engineering", Biomaterials, vol. 32, pp.87-94, Jan. 2011.

* cited by examiner

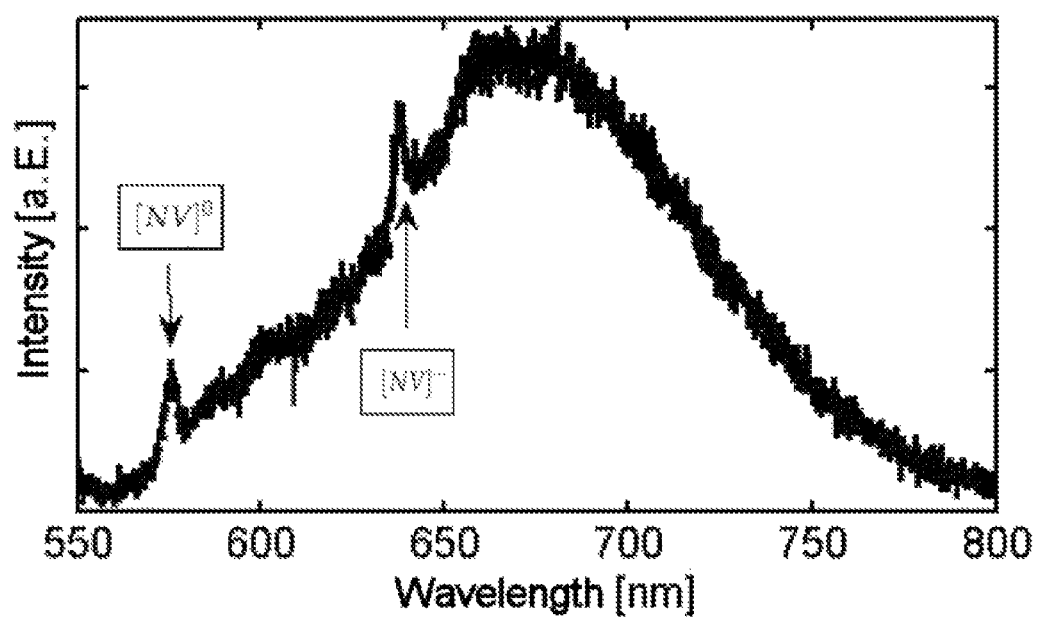

RESORBABLE IMPLANT MATERIAL MADE FROM MAGNESIUM OR A MAGNESIUM ALLOY

FIELD OF THE INVENTION

The present invention relates to an implant material made of magnesium or magnesium alloy and to a process for the production thereof.

BACKGROUND OF THE INVENTION

Both in veterinary and in human medicine the treatment of fractures in weight-bearing long bones employs medical implants made of medical steel or titanium. However, in their mechanical characteristics these implants are more rigid than bones and this can result in the phenomenon of stress shielding. For these and further reasons such implants are generally removed again after they have fulfilled their function which can be debilitating for the patient on account of the required anaesthesia and renewed tissue trauma.

Resorbable implants are of increasing interest for fracture treatment. The objective here is that the implants undergo a stress adjustment through a slow decrease in their stability with increasing strength of the healing bone. Optimal use of the hitherto available resorbable implants made of different polymers has not yet been accomplished on account of their low strengths at the stressed bone. By contrast, compared to other metallic implant materials magnesium and its alloys have a bone-like modulus of elasticity and favorable tensile and compressive strength. Magnesium and its alloys have higher strengths and a greater modulus of elasticity than resorbable polymers and are therefore the focus of scientific research. Bioresorbable implants, in particular made of magnesium or a magnesium alloy, for treatment of bone fractures are known for example from EP 2 318 057 B1 and the publications cited therein or from DE 10 2005 060 203 A1.

Resorbable implants are not only employed for fracture treatment. Implants made of magnesium and its alloys are today very often used as stents for the treatment of stenoses (vascular constrictions). Stents have a tubular or hollow-cylindrical base lattice open at both longitudinal ends. The tubular base lattice of such an endoprosthesis is introduced into the vessel to be treated and serves to support the vessel. Biodegradable stents made of magnesium or magnesium alloy are known from EP 2 198 898 B1 and publications cited therein.

However, the disadvantage of the known implants is that their resorption has hitherto only been trackable using x-ray or CT examinations. These examinations are comparatively complex and costly. The present invention has for its object to provide an implant material made of magnesium or magnesium alloy and a process for the production thereof, whose resorption in the body of the patient may be tracked in simple fashion without the need for x-ray or CT examinations.

SUMMARY OF THE INVENTION

The object is achieved by an implant material comprising homogeneously distributed fluorescent nanodiamonds having nitrogen-vacancy centers in a matrix of magnesium or a magnesium alloy, wherein the fluorescent nanodiamonds have nitrogen-vacancy centers (NV centers) which after excitation by a 532 nm laser beam have a detectable fluorescence band centered at a wavelength between 650 nm and 700 nm. The object is also achieved by a process for producing an implant material, wherein magnesium or a magnesium alloy is melted, fluorescent nanodiamonds having nitrogen-vacancy centers are added to the melt and the melt of magnesium or magnesium alloy provided with nanodiamonds is subjected to an ultrasound treatment.

DETAILED DESCRIPTION OF THE INVENTION

Brief Description of the Drawing

FIG. 1 is a graph showing the fluorescence spectrum of an NV-center in a nanodiamond at room temperature, excited by a 532 nm laser beam.

Fluorescent nanodiamonds (FNDs) are known as protein markers for example from K. Merchand and S. K. Sarkar, IEEE JOURNAL OF SELECTED TOPICS IN QUANTUM ELECTRONICS, VOL. 22, NO. 3, MAY/JUNE 2016. These have hitherto been used in research for visualizing biological cell processes. Fluorescent nanodiamonds are biologically nonhazardous and provide a stable emission in the near infrared range due to the nitrogen-vacancy centers (NV centres).

The NV center in the diamond is formed by a nitrogen atom, which substitutes a carbon atom in the diamond lattice, and a directly adjacent vacancy in the diamond lattice. This vacancy allows the NV centers to assume a negative ($NV^-$ center) or neutral ($NV^0$ center) charge. The NV center in the diamond has exceptional photophysical characteristics.

In the context of bioimaging the exceptional property of the negatively charged $NV^-$ center is that it may be optically excited between 480 nm and 580 nm to emit a broad luminescence band centered at around 700 nm. The excited state lifetime is approximately 17 ns, as described in J. M. Say, "*Luminescent Nanodiamonds for Biomedical Applications*", Biophys. Rev. (2011) 3:171-184. The neutral $NV^0$ center emits a relatively sharp line at 637 nm.

The production of fluorescent nanodiamonds having nitrogen vacancies is described for example in US 2014/0065424 A1 or WO 2017/108655 A1 which are hereby fully incorporated by reference.

To produce the fluorescent nanodiamonds having nitrogen-vacancy centers its crystal lattice must be damaged under controlled conditions to form these nitrogen vacancy centers without which optical imaging would not be possible. This is most commonly carried out by irradiation of nanodiamonds with fast ions in particle accelerators such as with an electron beam at an acceleration energy between 7 MeV and 15 MeV in the processes in US 2014/0065424 A1. These accelerated ions are capable of knocking carbon atoms out of the crystal lattice of a nanodiamond, thus leaving holes which are described as vacancies and at high temperatures are coupled with the nitrogen atoms present in the crystal as impurities. In place of costly and expensive irradiation in an accelerator more recent processes utilize irradiation in a nuclear reactor which is much faster and far less costly. To this end the nanorystals must initially be dispersed in molten boron oxide and then subjected to neutron radiation in a nuclear reactor. Neutron capture by boron nuclei generates a dense shower of helium and lithium ions which have the same effect in the nanocrystals as the ions generated in an accelerator: the controlled generation of crystal defects.

In one embodiment of the present invention the fluorescent nanodiamonds have a concentration of nitrogen-vacancy centers of more than 10 ppm, preferably more than 20 ppm, more preferably more than 25 ppm, determined by epifluorescence after excitation by a 532 nm laser beam. The method of determining the concentration of nitrogen-vacancy centers in a nanodiamond using epifluorescence after excitation by a 532 nm laser beam is described for example in Chi-Chen Fu et al. "Characterization and application of single fluorescent nanodiamonds as cellular biomarkers", PNAS, Vol. 194, Nr. 3, 727-732 (2007) which is hereby fully incorporated by reference. The concentration of nitrogen-vacancy centers is in particular determined by comparison of the intensity of the measured fluorescence with the intensity of the fluorescence of "single defect" diamonds (see cited literature in Chi-Chen Fu et al.). Such data are published for example in F. Treussart et al. (2006) Physica B Condensed Matter 376:926-929.

Fluorescent nanodiamonds which fulfill these characteristics are also commercially obtainable for example from Sigma-Aldrich Chemie GmbH, Steinheim, Germany.

Suitable light sources for investigating the transmission properties include any light source capable of activating the NV centers, for example a helium-neon laser whose wavelength of 632.7 nm approximately corresponds to the ZPL of the NV spectrum or a solid-state laser (JL-LD532-GTE; Jetlser) operated at a wavelength of 532 nm.

FIG. 1 shows the fluorescence spectrum of an NV-center in a nanodiamond at room temperature, excited by a 532 nm laser beam. The FIGURE shows a broad fluorescence band centered at a wavelength of about 700 nm.

The inventive implant material made of magnesium or magnesium alloy and containing homogeneously distributed fluorescent nanodiamonds may be produced by casting. It may subsequently be extruded or processed into implant articles by powder metallurgy processes such as MIM technology. Resorption of the implant material in the body of the patient causes the fluorescent nanodiamonds to pass into the blood circulation where they may be detected by fluorescence spectroscopy or by other means. The fluorescent nanodiamonds are gradually excreted from the body. This affords a wash-in/wash-out profile in the plasma which after calibration allows conclusions to be drawn about the resorption of the implant material.

When magnesium alloy is used as the matrix material it is preferable to employ alloying elements not considered hazardous to health. It is preferable to employ magnesium alloys with alloying elements selected from the group consisting of lithium, calcium, potassium, strontium, barium, scandium, yttrium, lanthanum, praesodymium, neodymium, samarium, europium, gadolinium, dysprosium, silicon, copper, zinc, gallium, gold, silver, bismuth, iron and combinations thereof. It is more preferable to employ magnesium alloys such as are described in DE 10 2016 007 176 A1 or DE 10 2016 119 227 A1 which are hereby fully incorporated by reference.

According to the invention the implant material is produced when magnesium or magnesium alloy is melted, nanodiamonds are added to the melt and the melt of magnesium or a magnesium alloy provided with nanodiamonds is subjected to an ultrasound treatment.

Such a process for homogeneous distribution of nanoparticles in a melt of magnesium or magnesium alloy is described in the article by H. Dieringa et al. "*Ultrasound Assisted Casting of an AM60 Based Metal Matrix Nanocomposite, Its Properties, and Recyclability*" in Metals 2017, 7, 338 which is hereby fully incorporated by reference.

In a preferred process for producing the implant material according to the invention magnesium or a magnesium alloy is preferably melted in a permanent mold in a furnace under protective gas and with stirring in a first step, the melt is admixed with the nanodiamonds in a second step and the nanodiamonds introduced into the melt are dispersed and deagglomerated using a sonotrode in a third step. It is further preferred when after removing the stirrer and the sonotrode the permanent mold containing the melt is immersed in a water bath. This brings about solidification of the melt from "bottom to top", thus avoiding cavity formation.

The thus produced implant material may subsequently be subjected to further processes by conventional means. For example the implant material may be remelted and then poured into the desired mold to form an implant article. Material may also be extruded to fabricate implants from the extrudate. The implant material may also be further processed into powder and then further processed into an implant article by metal injection molding (MIM).

The implant material according to the invention preferably comprises homogeneously distributed fluorescent nanodiamonds in a matrix of magnesium or magnesium alloy in an amount of 0.1% to 5% by weight, preferably 0.5% to 1.5% by weight, based on the weight of magnesium/magnesium alloy. The nanodiamonds preferably have a particle size of 1 to 20 nm, preferably 3 to 8 nm.

As described, to produce the implant material according to the invention the magnesium or the magnesium alloy is preferably melted in a permanent mold in a furnace under protective gas and with stirring in a first step, as described in H. Dieringa et al. "*Ultrasound Assisted Casting of an AM60 Based Metal Matrix Nanocomposite, Its Properties, and Recyclability*" in Metals 2017, 7, 338. The melt is preferably stirred mechanically, preferably at 150 to 250 rpm. The fluorescent nanodiamonds are then added to the melt. After addition of the fluorescent nanodiamonds the melt is treated with ultrasound. This is preferably achieved by introducing a sonotrode into the melt. The ultrasound treatment is preferably carried out over a period of 1 min to 10 min, more preferably 2 min to 5 min.

It is preferable when after the mixing and the ultrasound treatment the stirrer and the sonotrode are removed and the permanent mold is slowly lowered from the furnace into a water bath where the melt solidifies.

The thus produced implant material may subsequently be subjected to further processing by conventional means. For example the implant material may be remelted and then poured into the desired mold to provide a metallic implant article. The implant material according to the invention may also be extruded and an implant article may be fabricated from the extrudate.

The implant material according to the invention may also be processed into a metallic implant article using MIM technology. Use of MIM technology allows small, complex and precisely shaped metal components to be fabricated in near net shape. MIM technology belongs to the group of so-called powder metallurgy processes in which the starting material for the component to be produced is fine metal powder rather than a solid metal body. MIM stands for metal injection molding. In the MIM process the metal powder is made flowable by addition of thermoplastic binders and the flowable mixture is introduced into an injection mold. After molding the binder fraction is removed again and the component is sintered. Magnesium components may be produced using MIM technology by the process described in M. Wolff et. al. "*Magnesium powder injection moulding for*

*biomedical application*", Powder Metallurgy, 2014 (Vol. 57, No. 5), 331-340 which is hereby fully incorporated by reference.

When using MIM technology the binder provides for temporary bonding during the primary shaping/molding and ensures the stability of the component until final compacting of the metal powder by sintering. A portion of the binder is generally already removed before sintering, for example using a solvent (solvent debindering). The remainder of the binder decomposes at temperatures of about 300° C. to 500° C. and escapes in gaseous form during thermal debindering.

The invention claimed is:

1. An implant material comprising homogeneously distributed fluorescent nanodiamonds having nitrogen-vacancy centers in a matrix of magnesium or a magnesium alloy, wherein the fluorescent nanodiamonds have nitrogen-vacancy centers (NV centers) which after excitation by a 532 nm laser beam have a detectable fluorescence band centered at a wavelength between 650 nm and 700 nm.

2. The implant material as claimed in claim 1, wherein the fluorescent nanodiamonds have a concentration of nitrogen-vacancy centers of more than 10 ppm, determined by epifluorescence after excitation by a 532 nm laser beam.

3. The implant as claimed in claim 1, wherein the fluorescent nanodiamonds have a particle size of 1 to 20 nm.

4. The implant as claimed in claim 3, wherein the fluorescent nanodiamonds have a particle size of 3 to 8 nm.

5. A method for producing an implant material according to claim 1, wherein magnesium or a magnesium alloy is melted, nanodiamonds are added to the melt and the melt of magnesium or a magnesium alloy provided with nanodiamonds is subjected to an ultrasound treatment.

6. The method as claimed in claim 5, wherein the magnesium or the magnesium alloy is melted in a permanent mold in a furnace under protective gas and with stirring in a first step, the melt is stirred mechanically, the fluorescent nanodiamonds are then added to the melt and after addition of the fluorescent nanodiamonds the melt is treated with ultrasound.

7. The method as claimed in claim 6, wherein the ultrasound treatment is carried out using a sonotrode introduced into the melt.

8. The method as claimed in claim 5, wherein the ultrasound treatment is carried out over a period of 1 min to 10 min.

9. The method as claimed in claim 8, wherein the ultrasound treatment is carried out over a period of 2 min to 5 min.

10. The method as claimed in claim 6, wherein after the ultrasound treatment the mold is transferred into a water bath where the melt solidifies.

11. The method as claimed in claim 5, wherein the implant material is remelted and subsequently poured into the desired mold to afford a metallic implant.

12. The method as claimed in claim 5, wherein the implant material is extruded and the extrudate serves as a precursor for fabrication of an implant.

13. The method as claimed in claim 5, wherein the implant material is converted into a metallic implant using MIM technology.

14. A method for determining the degree of resorption of an implant material in a patient comprising detecting a fluorescence signal in the patient's blood, wherein the implant material comprises homogeneously distributed fluorescent nanodiamonds having nitrogen-vacancy centers in a matrix of magnesium or a magnesium alloy, wherein the fluorescent nanodiamonds have nitrogen-vacancy centres (NV centers) which after excitation by a 532 nm laser beam have a detectable fluorescence band centered at a wavelength between 650 nm and 700 nm.

15. The method of claim 14, wherein the fluorescent nanodiamonds have a concentration of nitrogen-vacancy centers of more than 10 ppm, determined by epifluorescence after excitation by a 532 nm laser beam.

16. The method of claim 14, wherein the fluorescent nanodiamonds have a particle size of 1 to 20 nm.

17. The implant material as claimed in claim 1, wherein the matrix material is magnesium and wherein the homogeneously distributed fluorescent nanodiamonds are present in an amount of 0.1% to 5% by weight based on the weight of magnesium in the matrix.

18. The implant material as claimed in claim 1, wherein the matrix material is magnesium alloy and wherein the homogeneously distributed fluorescent nanodiamonds are present in an amount of 0.1% to 5% by weight based on the weight of magnesium alloy in the matrix.

19. The method of claim 14, wherein the matrix material is magnesium and wherein the homogeneously distributed fluorescent nanodiamonds are present in an amount of 0.1% to 5% by weight based on the weight of magnesium in the matrix.

20. The method of claim 14, wherein the matrix material is magnesium alloy and wherein the homogeneously distributed fluorescent nanodiamonds are present in an amount of 0.1% to 5% by weight based on the weight of magnesium alloy in the matrix.

21. A method of treating fractures or stenoses, wherein an implant material comprising homogeneously distributed fluorescent nanodiamonds having nitrogen-vacancy centers in a matrix of magnesium or magnesium alloy is implanted in the body of a patient in need thereof,
   the fluorescent nanodiamonds having a detectable fluorescence band centered at a wavelength between 650 nm and 700 nm,
   and wherein degradation of the implant material is determined by fluorescence measurements of a sample of the patient's blood.

\* \* \* \* \*